(12) United States Patent
Winter et al.

(10) Patent No.: US 6,669,481 B2
(45) Date of Patent: Dec. 30, 2003

(54) NEUROCOGNITIVE ASSESSMENT APPARATUS AND METHOD

(75) Inventors: Kathryn P. Winter, Pensacola Beach, FL (US); Dennis L. Reeves, San Diego, CA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/140,376

(22) Filed: May 8, 2002

(65) Prior Publication Data

US 2003/0032866 A1 Feb. 13, 2003

Related U.S. Application Data

(60) Provisional application No. 60/289,116, filed on May 8, 2001, and provisional application No. 60/331,107, filed on Nov. 8, 2001.

(51) Int. Cl.[7] .............................. A61B 5/00; G09B 19/00
(52) U.S. Cl. ....................... 434/236; 600/300; 128/897; 128/920; 434/118
(58) Field of Search ................................. 434/118, 186, 434/156–157, 167, 169, 219–220, 227, 231, 236–238, 247, 258, 262, 276, 307 R, 308, 314, 322, 324, 327, 332, 335, 336, 350, 353, 362, 365, 354; 600/300–301, 587, 595, 544–545, 559, 26; 128/903–905, 920, 922–923, 897, 898; 273/430, 459, 460, 461, 236, 237; 380/2; 463/1; 705/26, 27; 706/924, 927

(56) References Cited

U.S. PATENT DOCUMENTS 6,066,092 A * 5/2000 Cady et al. .................. 600/300
6,280,198 B1 * 8/2001 Calhoun et al. ............ 434/236

* cited by examiner

Primary Examiner—Max F. Hindenburg
Assistant Examiner—Michael Astorino
(74) Attorney, Agent, or Firm—Elizabeth Arwine

(57) ABSTRACT

A neurocognitive assessment device is provided including a library of computer implemented neurocognitive tests. Each neurocognitive test is provided with a performance module, an instruction module and a correction module. The performance module generates a plurality of stimuli on a computer screen to which a test subject is prompted to respond. If the test subject produces N consecutive incorrect responses, the correction module automatically interrupts the test operation and displays test instructions on screen.

1 Claim, 13 Drawing Sheets

Subject Information

Name: _____  ID: _____  Battery: _____

Age: ☐  Sex: ☐  Race: _____  Occupation: _____  Hand Preference: ☐

Years of Education: ☐

Diagnostic Code 1: _____  Diagnostic Code 2: _____

Medications: _____

Other 1: _____  Other 2: _____  Other 3: _____

Comments:
_____
_____

[ ✓ Save ]   [ ✗ Cancel ]

FIG. 2

Choose one of the statements below
that best describes how you feel.

HOW DO YOU FEEL RIGHT NOW?

1. Feeling active and vital; alert; wide awake.

2. Functioning at a high level, but not at peak, able to concentrate.

3. Relaxed; awake, reponsive, but not at full alertness.

4. A little foggy; let down; not at peak.

5. Foggy; slowed down; beginning to lose interest in remaining awake.

6. Sleepy; woozy; prefer to be lying down; fighting sleep.

7. Almost in reverie; sleep onset soon; losing struggle to remain awake.

FIG. 3

Does the word below
describe how you feel?

Miserable

1 = Yes or Mostly

2 = Somewhat or Moderately

3 = No, Not at All

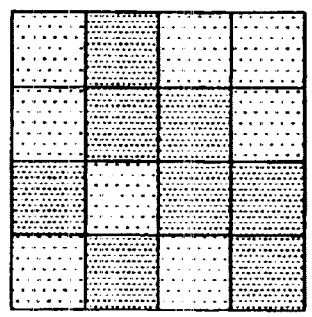
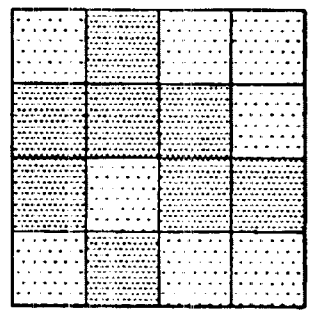
FIG. 13

NEUROCOGNITIVE ASSESSMENT APPARATUS AND METHOD

CROSS-REFERENCE TO RELATED APPLICATIONS

This application claims priority from provisional application Serial No. 60/289,116, filed May 8, 2001 and from provisional application Serial No. 60/331,107, filed Nov. 8, 2001, each of which is hereby incorporated by reference.

STATEMENT REGARDING FEDERALLY SPONSORED RESEARCH

Not Applicable.

BACKGROUND OF THE INVENTION

1. Field of the Invention

This invention relates generally to the field of neuropsychology. More particularly, this invention relates to measurement and assessment of cognitive performance.

2. Description of Related Art

For years neurology professionals have studied the effects that changes in brain conditions have on a person's cognitive abilities. Tests have been developed for measuring, e.g., simple and complex attentions/reaction, working memory, short-term memory and new learning, incidental memory, adaptive problem solving, continuous performance and spatial abilities.

Many cognitive test instruments are designed for single assessment situations or to answer specific diagnostic questions or to measure a specific cognitive skill, and often make use of the novelty of the test. These are rarely good for doing more than a few assessments because the subject may benefit from second and subsequent repetitions of the test making normative data (based on the single test administration) inappropriate.

In addition, many test instruments are specifically designed for subjects functioning at a specific level and do not work well with patients who are not functioning at that level. For example, typically a test that is useful for a high functioning group of subjects such as jet pilots may be less than ideal for a low functioning group such as stroke or Alzheimer's patients.

Accordingly, there is a need for a universal neurocognitive testing device and method that can accommodate patients functioning within a wide spectrum of cognitive levels. There is also a need for a test instrument and method that can reliably detect the deviation in patient's cognitive level over time.

SUMMARY OF THE INVENTION

It is an object of the invention to provide a neurocognitive testing device including a library of tasks for indexing patient's cognitive levels.

It is another object of the invention to provide a neurocognitive testing device that may be used for subjects with various cognitive abilities.

It is still another object of the invention to provide computer-implemented neurocognitive testing device that allows a clinician to modify testing parameters without modifying program code.

It is yet another object of the invention to provide computer implemented neurocognitive tasks having variable task parameters.

It is a further object of the invention to provide a library of computer implemented neurocognitive tasks that correct for the subject's misunderstanding of task instructions.

BRIEF DESCRIPTION OF THE FIGURES

FIG. 2 is a graphical user interface for the apparatus of the present invention.

FIG. 3 is an exemplary screen shots showing one of the tests of the invention.

FIG. 4 depicts an exemplary screen shot of still another test administered in accordance with the invention.

FIG. 8 illustrates an exemplary screen shot of another test of the invention.

FIG. 13 illustrates a screen shot of still another test of the present invention.

DETAILED DESCRIPTION OF THE INVENTION

Figure 1:
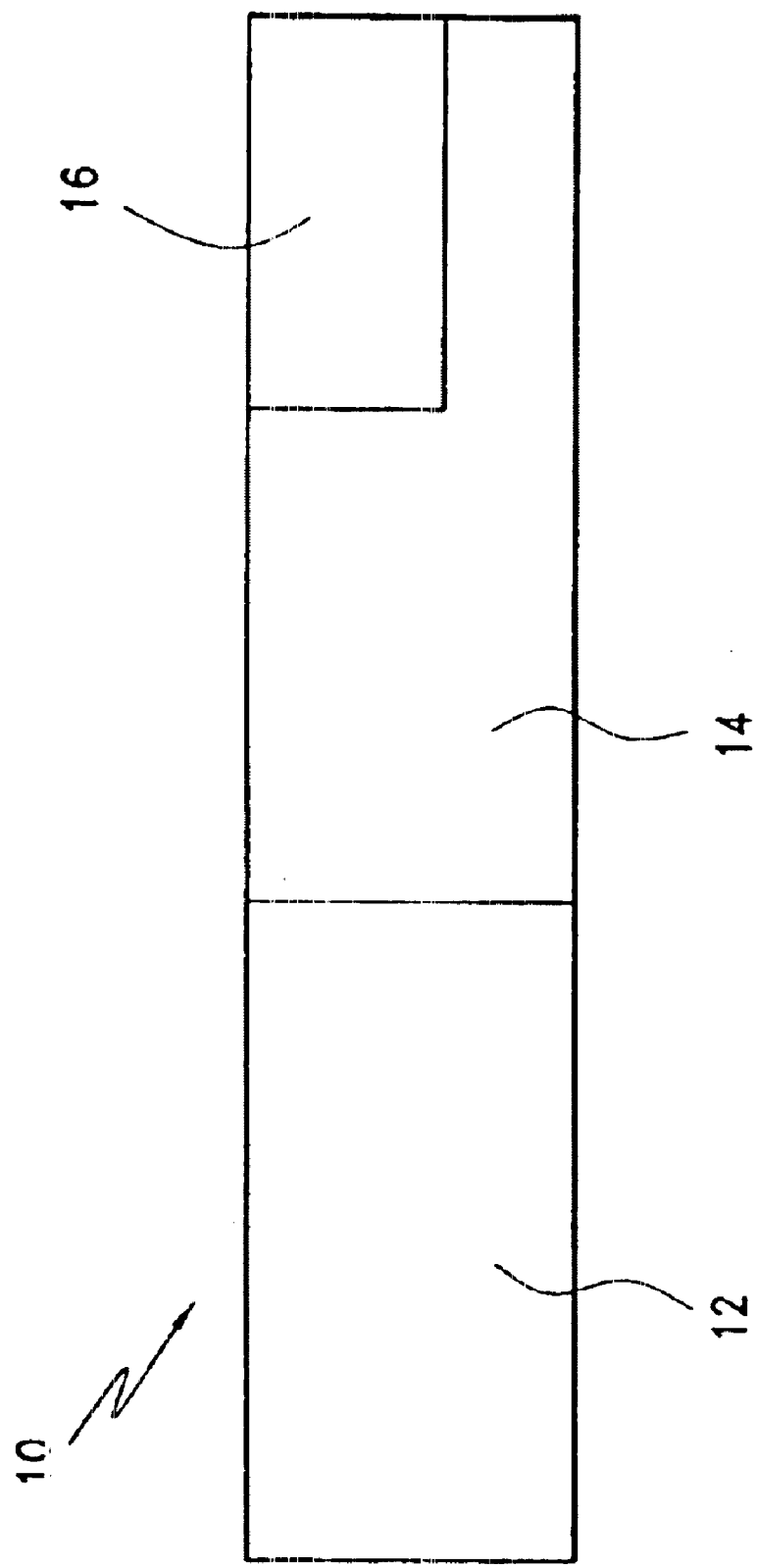
FIG. 1 is a block diagram of a neurocognitive assessment device according to the present invention.

The present invention includes a plurality of components including a library of neurocognitive tasks, a menu program, a statistical analysis program and a graphics program. The components may function individually or in concert with one another. The library of neurocognitive tasks comprises a plurality of computer-implemented tasks designed to index or assess cognitive skills. Many of the tasks include switches that facilitate alteration of certain parameters of the task by the test administrator without modifying the underlying program code thus making the tasks useful for indexing multiple cognitive skills. In addition, in some embodiments, each task includes an instruction module and a performance module. The instruction module provides instructions to the test subject for implementing the task. The test subject interacts with the performance module to carry out the task.

The menu program allows the test administrator to select one or more tasks to be performed from the library and to customize parameters of those tasks altering the switches.

The statistical analysis program collects, interprets and analyzes data generated by performance of the tasks and the graphics program displays the data such that the data may be readily interpreted by a clinician.

As will be appreciated by one of skill in the art, the present invention may be embodied as a computer implemented method, a programmed computer, a data processing system, a signal, and/or computer program. Accordingly, the present invention may take the form of an entirely hardware embodiment, an entirely software embodiment or an embodiment combining software and hardware aspects. Furthermore, the present invention may take the form of a computer program on a computer-usable storage medium having computer-usable program code embodied in the medium. Any suitable computer readable medium may be utilized including hard disks, CD-ROMs, optical storage devices, or other storage devices.

Computer program code for carrying out operations of the present invention may be written in a plurality of languages. In a preferred embodiment of the invention, the computer program code is written in C++ BUILDER®.

The program code may execute entirely on the user's or test subject's computer, as a stand-alone software package, or it may execute partly on the user's computer and partly on a remote computer. In the latter scenario, the remote computer may be connected directly to the user's computer via a LAN or a WAN (Intranet), or the connection may be made indirectly through an external computer (for example, through the Internet).

The present invention is described below with reference to flowchart illustrations of methods, and block diagrams of apparatus (systems) and computer programs in accordance with the several embodiments of the invention. It will be understood that each block of the flowchart illustrations and block diagrams, and combinations of blocks in the flowchart illustrations and block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means or program code that implements the function specified in the flowchart block or blocks.

The computer program instructions may also be loaded, e.g., transmitted via a carrier wave, to a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Various templates, program code and the database(s) according to the present invention may be stored locally on a provider's stand-alone computer terminal, such as a desktop computer, laptop computer, palmtop computer, or personal digital assistant (PDA) or the like. Exemplary stand-alone computers may include, but are not limited to, APPLE®, SUN MICROSYSTEMS®, IBM®, or IBM®-compatible personal computers. Accordingly, the present invention may be carried out via a single computer system, such as a desktop computer or laptop computer. Preferably, the present invention is implemented using an IBM®-compatible computer system having minimum specifications of a PENTIUM® 90 MHz microprocessor, at least 32 MB RAM, at least 4 MB free disk space. The present invention is preferably implemented using the WINDOWS® 95/98/2000 or NT4.0 operating systems.

The present invention is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. The accompanying drawings show preferred embodiments of the invention.

In keeping with the invention, a library of neurocognitive tasks is provided for measuring performance degradation from injury, illness, fatigue, medications, chemical exposure, radiation or for measuring any other perceived cognitive loss or gain. The library includes several known neuropsychological tests that have been modified for computer implementation as well as some newly developed neuropsychological tests. The tests include but are not limited to the following: 1) The Stanford Sleepiness Scale, 2) The Mood Scale 2-R, 3) Simple Reaction Time Test, 4) Memory Search Test, 5) Running Memory and Continuous Performance Test, 6) Mathematical Processing Test, 7) Digit Set Comparison Test, 8) Logical Reasoning—Symbolic Test, 9) Code Substitution and Memory Tests, 10) Spatial Processing Test, and 11) Matching to Sample Test. While each test in the library is unique, there are also several common attributes to each test.

As illustrated in FIG. 1 and in keeping with an aspect of the invention, one or more of the tests 10 in the library may be provided with an instruction module 12 and a performance module 14. Instruction module 12 preferably includes program code for generating textual instructions on a computer screen for implementing performance module 14. Such instructions may include informing the test subject as to the type of input device, e.g., mouse, keyboard, button, touch-screen, etc., to be used to respond to stimuli and queries generated by the performance module. The instruction module may further include image files, e.g., .bmp, .jpeg, .gif, to augment or replace the textual instructions for assisting test subjects who have trouble reading the textual instructions.

In addition, instruction module 12 may include audio and/or audio-visual instruction sets. These instructions sets, which may be created or maintained with a common editor, can utilize the MICROSOFT® agent technology. Various agent characters may be used. The agent characters may be programmed to move and speak enhancing the quality and understanding of the test instructions and providing an avenue of appeal for testing audiences that are unique, i.e., children or the elderly. The test administrator may alter the movements and speech of the agent characters as desired.

Performance module 14 generates stimuli on the computer screen to which the test subject is prompted to respond. Such stimuli may be visual, aural or audio-visual. In keeping with an aspect of the invention, aural stimuli facilitate testing of individuals who are visually impaired. Aural stimuli may also be employed where the test administrator desires to mimic an environment in which the test subject cannot see a computer monitor.

In accordance with a particularly preferred aspect of the invention, correction module 16 may be provided with performance module 14. Correction module 16 monitors the first N responses to the first N stimuli generated by performance module 14, where N is an integer selected by the test administrator. If the first N responses are incorrect, correction module 16 interrupts the task and provides an indication that there may be a misunderstanding of the instructions, e.g., by displaying a message on the computer screen. Thereafter, instruction module 12 redisplays the instructions and performance module 14 restarts the task. After a predetermined number of successive task interruptions, performance module 14 stops the test and, preferably displays a message on the computer screen directing the test subject to contact the test administrator. In this manner, correction module 16 helps prevent accumulation of bad test data due to a lack of understanding of test instructions.

In accordance with another aspect of the invention, each test generates data that is may be processed by the statistical analysis program to generate mean/median, reaction time, accuracy and throughput.

For each test, the test subject may respond to stimuli using an input device such as a mouse, a keyboard, a touch screen, a dedicated response button or the like.

The library land the various tests comprising the library are described in more detail below.

Subject Information Demographic

This is a module provided with the library for collecting data relating to the test subject and creating a corresponding database. Preferably, this module provides a simple mechanism, e.g., GUI, for recording important participant demographic and medical information in a format that is compatible with database standards and with data produced by the test modules. While extremely useful, this module is optional with the various tests and batteries.

As illustrated in FIG. 2, the GUI includes the following data fields: Subject ID, battery identification, age, sex, race, occupation, hand preference, years of education, diagnostic code 1, diagnostic code 2, medications, and comments. The GUI and corresponding database may also be customized by the test subject to include up to three data fields that are preferably specific to the research or clinical purpose for administering the test.

Stanford Sleepiness Scale

This test is comprised of a series of statements that describe how one feels with respect to alertness or sleepiness. In a preferred embodiment, this test comprises seven descriptive statements. The module may display the statements to the test subject one at a time or all simultaneously. In any event, the test subject is directed to select the statement that best describes its feelings at that moment in time. The test subject may make the selection on screen using a mouse, the keyboard or any other known input device. The seven descriptive statements of the preferred embodiment are:

Feeling very alert, wide awake, and energetic.

Able to concentrate, but not quite at peak.

Relaxed, awake, responsive, but not fully alert.

A little foggy and mild difficulty concentrating.

Foggy, slowed down, beginning to lose interest in remaining awake.

Sleepy, woozy, prefer to be lying down; fighting sleep.

Sleep onset soon, losing struggle to remain awake.

An exemplary screen shot is illustrated in FIG. 3.

Mood Scale 2-R

This test is designed to assess either mood state or trait in test subjects in six subcategories that include Activity (high energy-level), Happiness (positive disposition), Depression (dysphoria), Anger (negative disposition), Fatigue (low-energy level), and Fear (anxiety level). The test includes a plurality of subscales, each including a plurality of adjectives.

In operation, the test subject is provided with an on-screen query and a variable response and indicia for the test subject to indicate either agreement or disagreement with the response. In preferred embodiments, the query remains constant for each subscale and the response varies among the plurality of adjectives linked to the subscale. Participants are asked to reply to the variable response by selecting the appropriate indicia, e.g., by pressing 1, 2, or 3 on the computer keyboard, (i.e., "press 1 for yes, 2 for somewhat, and 3 for no") in response to the query, "How does the word shown below describe how you feel right now." Once the participant has selected the appropriate indicia, the variable response is changed and the participant replies to the updated variable response. Scores for each of the six scales are produced and stored in a participant database.

The adjectives or responses linked to the Activity subcategory include energetic, lively, alert, spirited, active and steady. The adjectives linked to the Happiness subcategory include good, content, cheerful, satisfied, pleased and happy. The adjectives linked to the Depression subcategory include miserable, discouraged depressed sad, downcast and gloomy. The adjectives linked to the Anger subcategory are grouchy, enraged, annoyed, angry, furious and irritated. The adjectives linked to the Fatigue subcategory include inactive, weary, drowsy, tired, sluggish, and lazy. The adjectives linked to the Fear(anxiety) subcategory include uneasy, alarmed, insecure, afraid, nervous and anxious.

An exemplary screen shot of this test is illustrated in FIG. 4.

Simple Reaction Time

This is a test designed to provide a measure of pure reaction time, an important aspect of neurocognitive assessment. In operation, a simple stimulus is presented on screen and the participant is instructed to input a response each time the stimulus is presented. When the stimulus is presented, it remains on screen for a predetermined period of time hereinafter referred to as the RT period. The RT period may be adjusted as desired by the test administrator. For example, when testing a jet pilot it may be desirable to have a very short RT period which requires a quick response. However, when testing a subjects who's reflexes are not as keen, i.e., Alzheimer's candidates, it may be desirable to have a longer RT period thus allowing slower response times. Similarly, the presentation rate of the stimulus may be varied as desired by the administrator.

Figure 5:
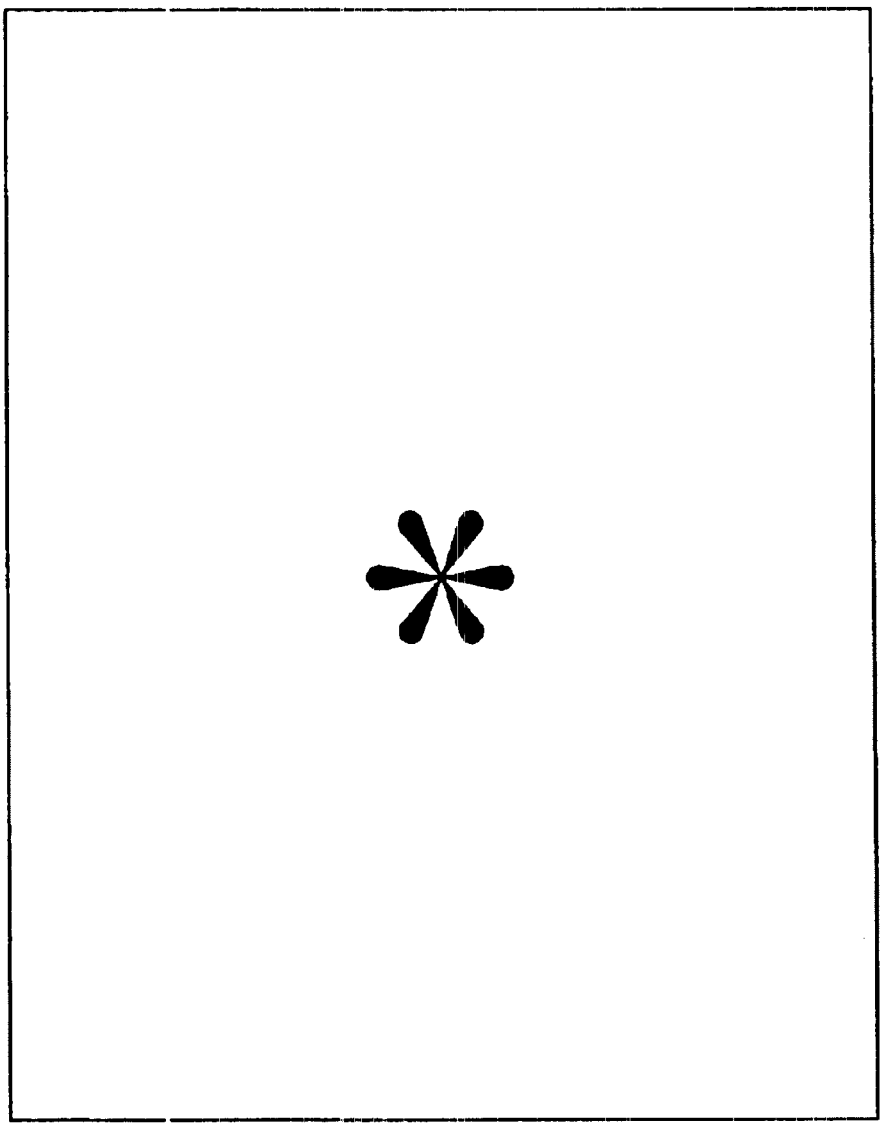
FIG. 5 illustrates an exemplary screen shot of yet another test of the invention.

An exemplary screen shot is depicted in FIG. 5.

2-Choice Reaction Time

This test is similar to the Simple Reaction Test except that two different stimulus characters are presented, e.g., "+" and "*". The pattern of presentation of the stimulus, the RT period and the rate of presentation may be adjusted by the test administrator as desired.

Memory Search (Sternberg RT & Symbolic)

This test is useful for indexing the subject's working memory. In accordance with the invention, a set of characters is displayed horizontally, preferably in the center of the monitor. The set of characters is referred to herein as the "memory set". The test subject should view the memory set until it is memorized. The memory set is preferably comprised of 2, 4, or 6 letters and/or symbols. However, the number of characters that comprise the memory set may be varied by the administrator to accommodate the testing environment.

After the memory set has been learned, the subject generates an input, e.g., presses a response key, to begin the test. During this part of the test, single "probe" (letters or symbols) are presented preferably in the center of the screen, and preferably one at a time. The subject indicates whether or not the probe matches any of the memory set items. Responses may be entered by pressing a specified key or mouse button. Each probe remains on the screen until the subject responds or until a pre-selected time limit has elapsed. The screen is cleared momentarily between successive probe presentations.

In keeping with a particularly preferred aspect of the inventions, each successive administration of the test uses a unique memory set. Memory set letters are selected randomly from the following list: A, B, C, E, F, G, H, I, J, K, L, M, Q, R, S, T, U, X, Y. The memory set characters are preferably centered horizontally in the middle of the screen with one character space between each letter. Positive probes, i.e., probes that match one of the memory set characters, are equally likely to match any of the memory set letters. Further, positive and negative probes (probes that do not match any of the memory set characters) are presented in an equal-probability randomized order.

In constructing the memory set, it is desirable to exclude characters that are similar in appearance. For example, in the preferred embodiment, the letters U and V were expressly excluded from the memory set so as not to be mistaken, one for the other.

Figure 6:
FIG. 6 shows an exemplary screen shot of a further test of the invention.

An exemplary screen shot is illustrated in FIG. 6.

Running Memory (Continuous Performance Test)

This test is intended to index the test subject's concentration level and attention span. The test requires the subject to continuously compare characters, e.g., numbers or symbols. In operation, characters are presented on screen one at a time, preferably in the center of the screen. In accordance with a preferred aspect of the invention, the characters are presented in a random order. Prior to being presented with the characters, test subjects are instructed to continuously monitor the characters and input a response using an input device if the character on screen matches the character that immediately preceded it. The test subject is instructed to input a different response, i.e., press another key or button, if the character on screen does not match the character that immediately preceded it.

Each character may be displayed on the screen for a period of time that may be selected by the test administrator prior to administration of the test. In addition, the test administrator may select/adjust the period of time between presentations of successive characters. For example, characters may be presented either after a predetermined time has elapsed or responsive to the subject's response input, whichever occurs first. In preferred embodiments, characters should be displayed as described in connection with this test for about five minutes to effectively assess the subject's concentration level and attention span.

Figure 7:
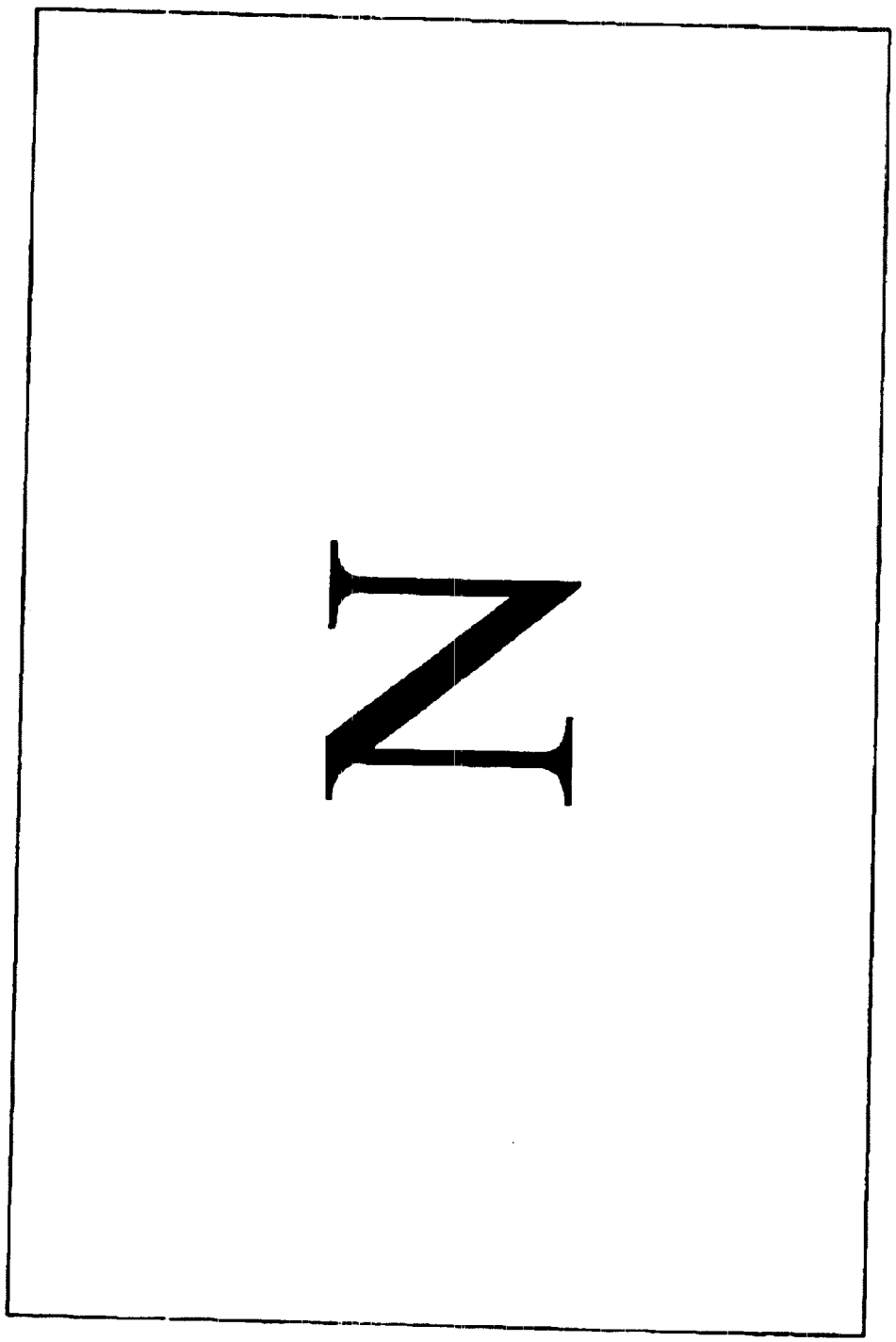
FIG. 7 depicts an exemplary screen shot of still a further test of the invention.

An exemplary screen shot is shown in FIG. 7.

Symbolic & Procedural Reaction Time (Modified Stres rt Tasks)

In this test, a variety of characters are presented on screen, one at a time and preferably in the center of the screen. In a preferred embodiment, four distinct characters are presented. For example, the characters may include shapes or alpha-numeric characters. The test subject is instructed to input a first specified response each time first and second characters are detected and to input a second specified response each time third and fourth characters are detected. The test subject may input its response by depressing specified keys on a keyboard, by selecting a specified input using a mouse, or by using any other known input procedure.

In accordance with an aspect of the invention, in one embodiment, the character quality is normal and the characters are presented at regular intervals. In accordance with another embodiment, the character quality is degraded and the characters are presented at regular intervals. In accordance with still another embodiment, the character quality is normal but the characters are presented at variable intervals.

Advantageously, the duration and period of the intervals may be controlled by the test administrator without reconfiguring program code.

Mathematical Processing

This test is used to assess the test subject's simple arithmetical and concentration abilities. In this test, arithmetic problems are presented on screen, preferably in the middle of the screen. The test requires the subject to deduce an answer and then decide if the answer is greater-than or less-than a specified number, e.g., the number five. Each problem includes two mathematical operations (addition and/or subtraction) on sets of three single-digit numbers (e.g., 5+3−4=?). The subject is instructed to read and calculate from left to right and indicate whether the answer is greater-than or less-than five by pressing one of two specified response buttons/keys. The operators and operandi are selected at random with the following restrictions: only the digits 1 through 9 are used; the correct answer may be any number from 1 to 9 except 5; greater-than and less-than stimuli are equally probable; cumulative intermediate totals have a positive value; working left to right the same digit cannot appear twice in the same problem unless it is preceded by the same operator on each occasion (e.g., +3 and +3 are acceptable, while +3 and −3 are not); and the sum of the absolute value of the digits in a problem must be greater than 5.

Figure 8:
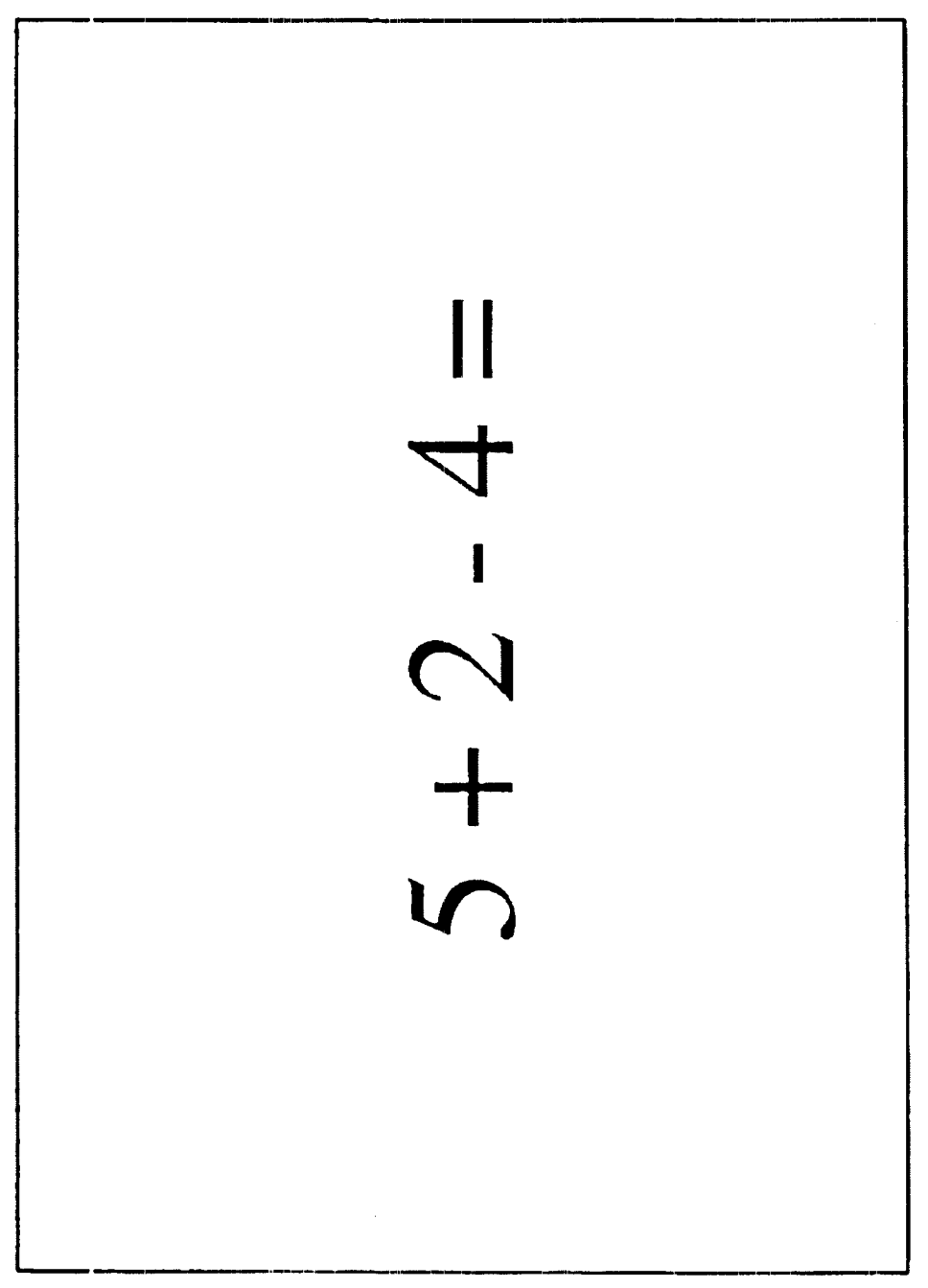

An exemplary screen shot is illustrated in FIG. 8.

Digit Set Comparison

This test is used primarily to index immediate memory and attention. In this test, a string of digits ranging in length from 2 to 10 numbers is presented in the center of the screen. After a specified period, the fist string of digits disappears and a second string is presented. The duration of the specified period is adjustable and may be controlled by the test administrator without alteration of the program code. The test subject is instructed to compare the two strings of digits and decide if they are the same digits and in the same order. The test subject is further instructed to respond providing an input.

Figure 9:
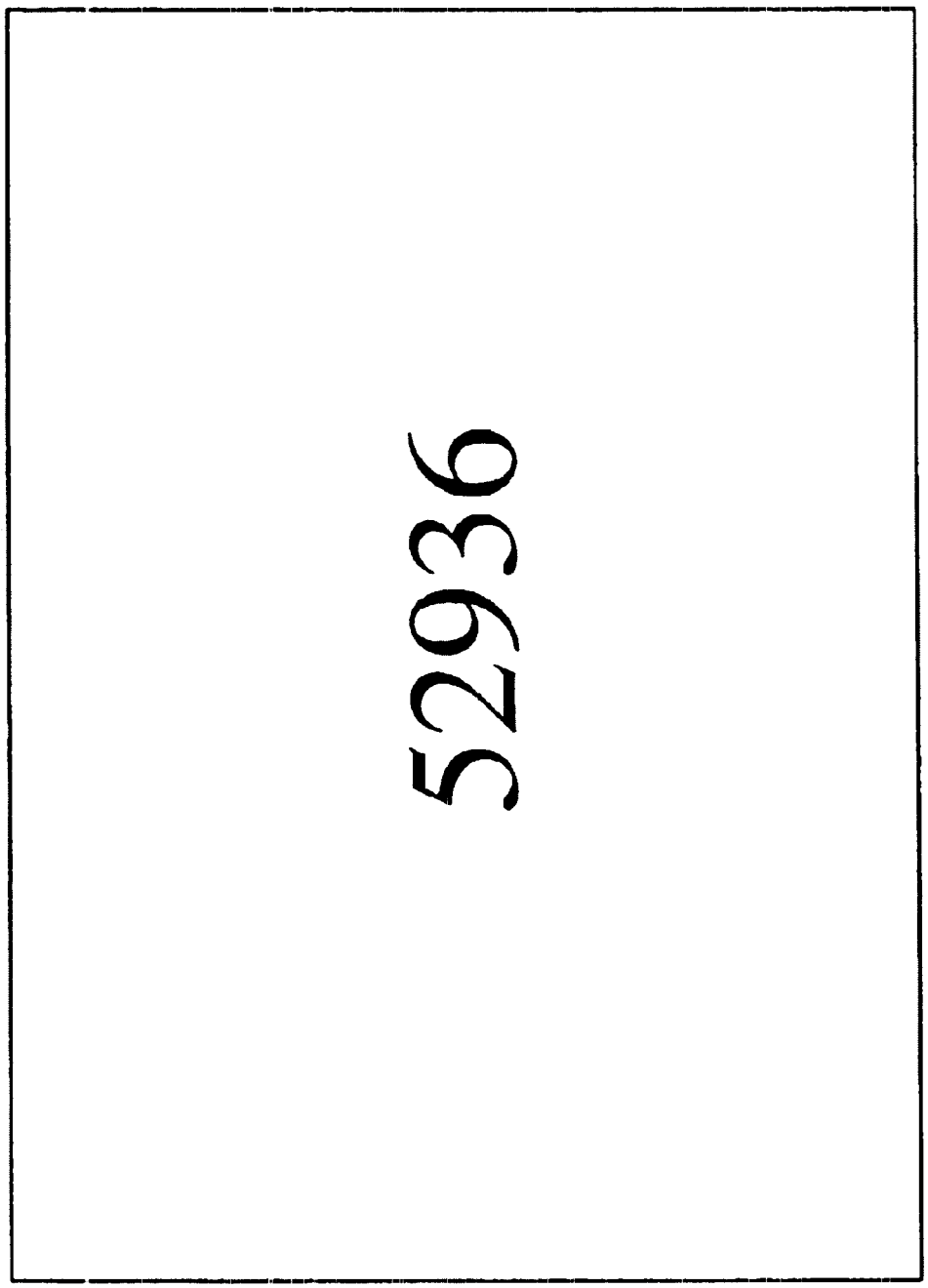
FIG. 9 shows an exemplary screen shot of still another test of the invention.

An exemplary screen shot is depicted in FIG. 9.

Logical Reasoning

This test is useful for indexing ability for abstract reasoning and verbal syntax. It is a linguistic task requiring knowledge of English grammar and syntax. It also requires the ability to determine whether various simple sentences correctly describe the relational order of two symbols. In this task, stimulus pairs may be presented one at a time and are preferably screen-centered rather than left-justified to reduce differences in visual search times.

On each trial the symbol pair "#&" or "&#" is displayed along with a statement that correctly or incorrectly describes the order of the letters as depicted in the example below:

&# is first

The subject is instructed to decide as quickly as possible whether the statement is true or false and then to provide an input indicating the response.

Figure 10:
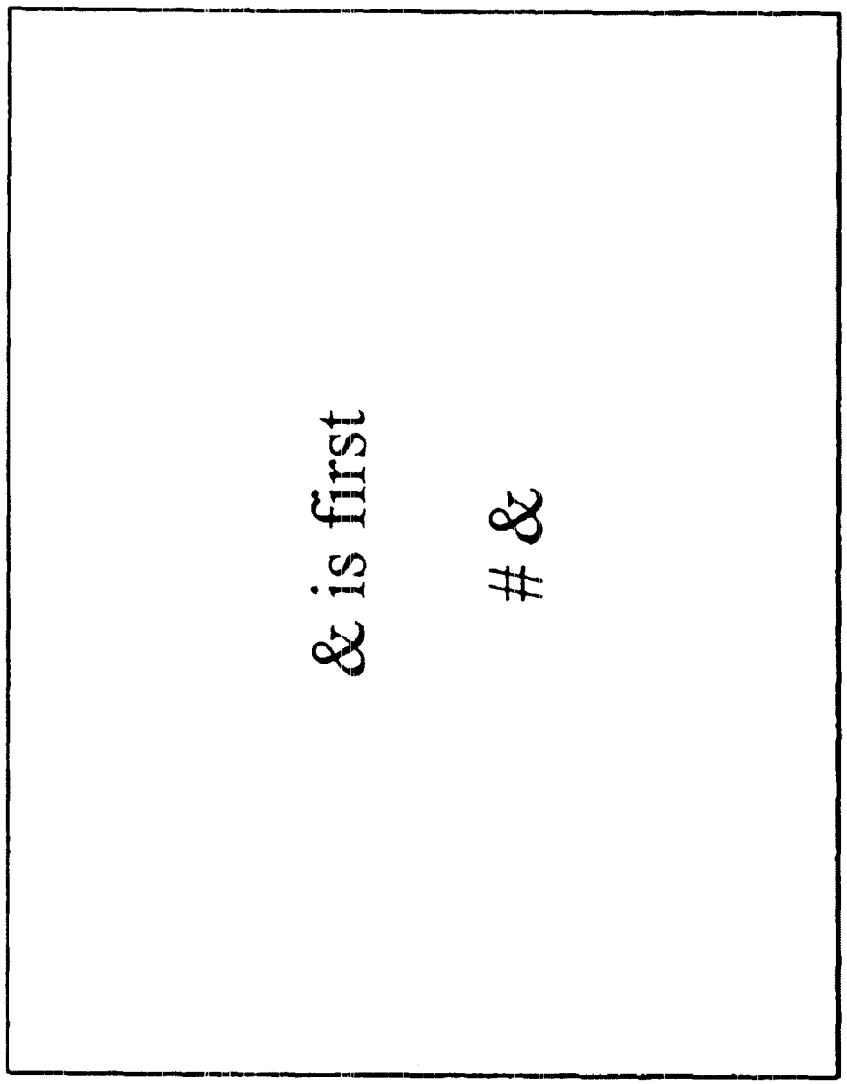
FIG. 10 illustrates a screen shot of yet another test of the invention.

An exemplary screen shot is illustrated in FIG. 10.

Code Substitution and Memory Test

Figure 11:
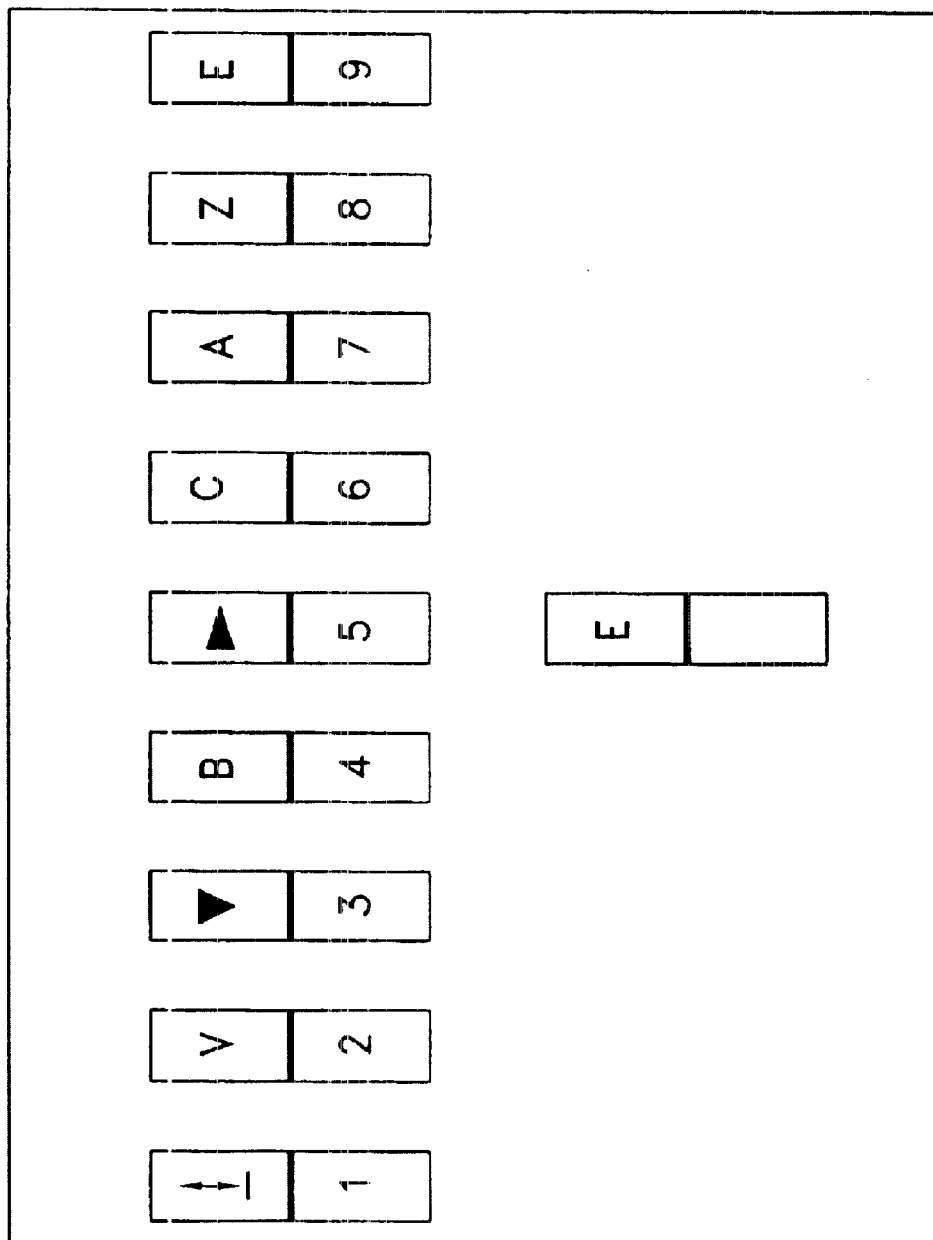
FIG. 11 depicts a screen shot of still another test of the present invention.

In this test, a string of preferably up to 9 symbols and 9 digits may be displayed across the upper portion of the screen and preferably arranged so that the digit string is immediately below the symbol string as illustrated in FIG. 11. There is one digit corresoonding to each symbol. During the test a test pair (a symbol and corresnonding digit) may be presented at the bottom of the screen, below the digit/symbol string. The goal of the test is to determine whether the test pair matches any associated pair in the string. The test taker may respond using an input device to indicate that the test symbol and digit are a correct or incorrect pairing.

The initial presentation is a visual scanning and learning procedure. The ratio of correct to incorrect displays is preferably 3:1 and each pair is preferably presented a minimum of 8 times yielding 6 correct presentations and two incorrect presentations per digit symbol set.

An association recognition memory recognition memory trial is then presented immediately and at a selected time interval following the learning trial. During this portion of the test, the procedure is essentially the same as the learning procedure. However, the comparison coding strings are not displayed. Only the test stimuli are presented and the subect has to indicate whether the displayed pair is correct or incorrect base on the subject's recollection of the paired associates presented during the learning trial. The ratio of correct to incorrect presentations during the associative recognition trial is preferably about 1:1 so there is about a 50% chance of being presented with a correctly matched symbol and digit pair.

Spatial Processing

Figure 12:
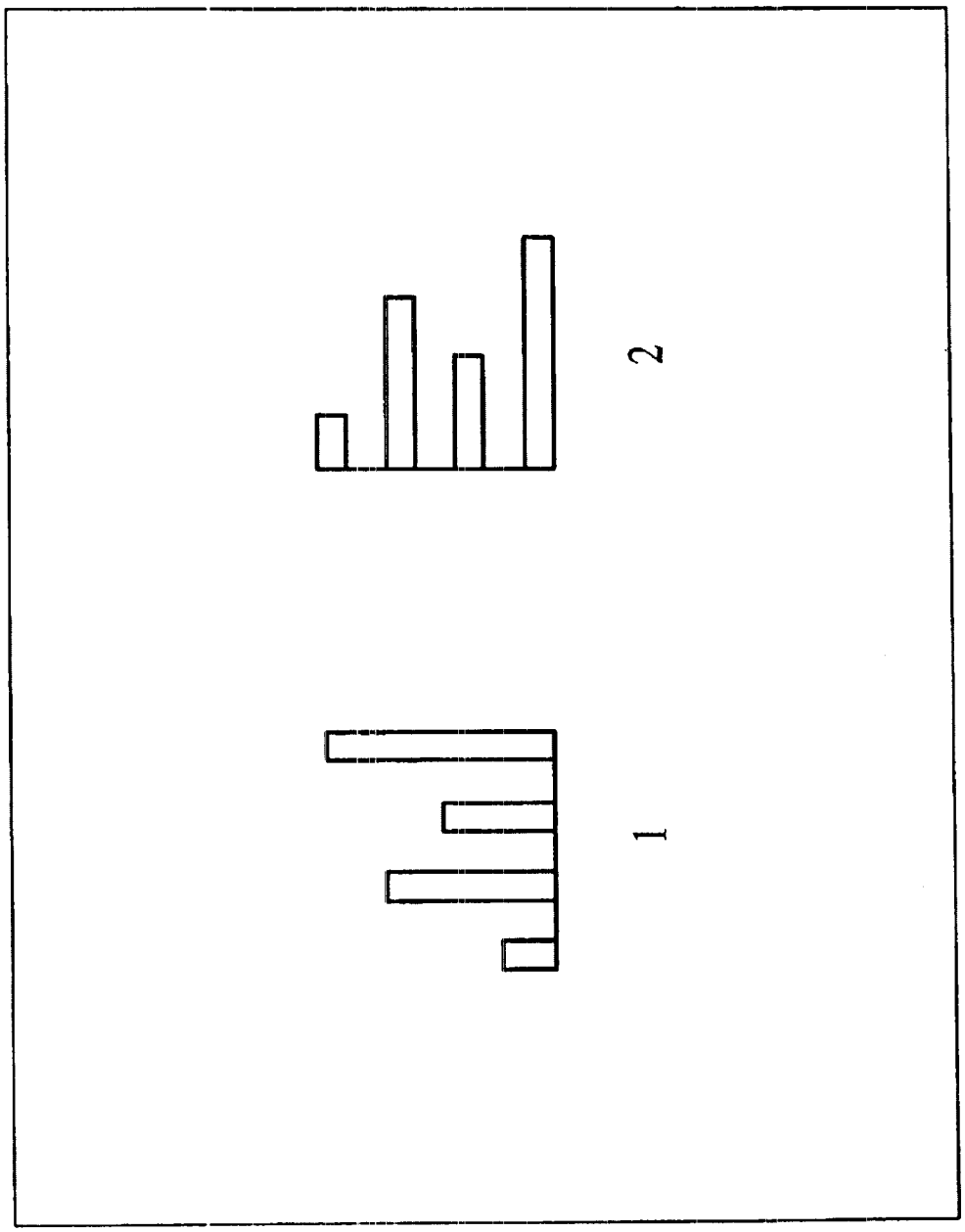
FIG. 12 shows a screen shot of a further test of the present invention.

In this test, as illustrated in FIG. 12, a pair of four bar histograms displayed as pairs and the subject is requested to determine whether they are identical. One histogram is preferably rotated either about 90° or about 270° with respect to the other histogram. The subject may respond to indicate that the two histograms are either the same or different using the input device.

Matching to Sample

In this test, the subject is asked to respond to stimuli that correspond in some fashion to a sample stimulus. In a preferred embodiment, a 4×4 matrix (checkerboard) is initially presented in the center of the screen as a sample stimulus to the subject. For each trial presentation of a matrix, the number of cells that are shaded may be varied at random from only one cell to 12 cells. When the subject responds via the input device or after a predetermined period of time, e.g., 30 seconds, the sample matrix is removed from the screen. Following a second predetermined time interval, e.g., 20 seconds, a set of two comparison matrices are presented side by side on the screen. One of the comparison matrices matches the sample matrix and the other comparison matrix preferably differs in shading from the sample by one cell. The subject's task is to indicate using the input device, which matrix matches the sample matrix.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A neurocognitive testing device comprising:

a performance module including program code instructions contained in a computer readable medium for administering a neurocognitive test including displaying stimuli on a computer screen and for receiving responses to the stimuli and generating test data based on the responses to stimuli;

a correction module including program code instructions contained in a computer readable medium for monitoring the responses to the stimuli and interrupting administration of the neurocognitive test when the first N responses are incorrect, where N is positive integer;

an instruction module including program code instructions contained in a computer readable medium for displaying instructions for responding to the stimuli on a screen responsive to interruption of administration of the neurocognitive test; and a neurocognitive statistical analysis module that displays test data such that the data may be interpreted by a clinician.

* * * * *